United States Patent
Buchalter

(10) Patent No.: US 7,665,893 B2
(45) Date of Patent: Feb. 23, 2010

(54) PROTECTIVE COVER SET FOR A MEDICAL PROBE

(75) Inventor: Neal Buchalter, Short Hills, NJ (US)

(73) Assignee: Parker Laboratories, Inc., Fairfield, NJ (US)

( * ) Notice: Subject to any disclaimer, the term of this patent is extended or adjusted under 35 U.S.C. 154(b) by 137 days.

(21) Appl. No.: 11/675,986

(22) Filed: Feb. 16, 2007

(65) Prior Publication Data
US 2008/0200754 A1 Aug. 21, 2008

(51) Int. Cl.
G01K 1/08 (2006.01)
A61B 1/00 (2006.01)

(52) U.S. Cl. .................. 374/158; 374/209; 374/E1.011; 600/101; 600/121

(58) Field of Classification Search ................. 374/158, 374/209, 163, 208, 183, 185, 179, 141, 100, 374/E1.011–E1.013, E1.016; 600/235, 200, 600/101, 121; 116/216
See application file for complete search history.

(56) References Cited

U.S. PATENT DOCUMENTS

| | | | | |
|---|---|---|---|---|
| 4,378,069 A | * | 3/1983 | Franco | 383/207 |
| 5,066,142 A | * | 11/1991 | DeFrank et al. | 374/208 |
| 5,224,543 A | * | 7/1993 | Watkins et al. | 166/279 |
| RE34,599 E | * | 5/1994 | Suszynski et al. | 374/158 |
| 5,466,898 A | * | 11/1995 | Gilbert et al. | 181/131 |
| 5,795,632 A | * | 8/1998 | Buchalter | 428/35.2 |
| 5,980,451 A | * | 11/1999 | O'Hara et al. | 600/121 |
| 6,022,140 A | * | 2/2000 | Fraden et al. | 374/158 |
| 6,390,671 B1 | * | 5/2002 | Tseng | 374/158 |
| 6,945,936 B1 | * | 9/2005 | Kerr | 600/406 |
| 7,111,728 B2 | * | 9/2006 | LeTourneau | 206/306 |
| 7,354,399 B2 | * | 4/2008 | Strom et al. | 600/200 |
| 7,458,932 B2 | * | 12/2008 | Sun | 600/190 |
| 2006/0105126 A1 | * | 5/2006 | Kendig | 428/35.2 |

\* cited by examiner

Primary Examiner—Gail Verbitsky
(74) Attorney, Agent, or Firm—Hahn, Loeser & Parks, LLP; William S. Nabors

(57) ABSTRACT

A protective cover set for a medical probe designated to be inserted into an endocavity or used intraoperatively in an incision of a human or an animal body, said cover set comprising a probe cover made from a film material, said probe cover having a mouth end with a mouth for inserting said probe and a closed end opposite to said mouth end; and an outer wrapper being joined to said probe cover, said outer wrapper covering at least a length of said probe cover; the probe cover comprising an adhesive element connected to said mouth end of said probe cover.

10 Claims, 3 Drawing Sheets

PROTECTIVE COVER SET FOR A MEDICAL PROBE

BACKGROUND OF THE INVENTION

1. Field of the Invention

The present invention relates to a protective cover set for covering a medical probe that may be inserted into an endocavity or used intraoperatively through an incision in a human or an animal body.

2. Background

For certain medical examinations, elongated probes are inserted into body cavities, i.e. endocavities, for positioning the probe relative to the body area to be examined. To protect the ultrasound probes against contamination from body fluids like sweat, blood, saliva, mucus, pus and other secretions, a protective cover may be used as described in U.S. Pat. No. 5,795,632. U.S. Pat. No. 5,795,632 has been assigned to the same assignee and is hereby incorporated by reference in its entirety.

For some applications of the protective cover set, the probe cover must be fixed securely to the medical probe, especially when the medical probe, e.g. an ultrasound probe, is moved within the endocavity.

It is known to use clamps or rubber bands to attach the probe cover to the ultrasound probe. However, clamps and rubber bands both require two hands to fix the probe cover to the ultrasound probe. This is inconvenient and time-consuming. Further, clamps and rubber band may shift relative to the probe cover and therefore do not provide a secure hold.

SUMMARY OF THE INVENTION

One object of the invention is to develop a protective probe cover set for a medical use, whereby a suitable adhesive element provides for easy handling and allows for one hand use of the probe cover.

In some embodiments, the invention facilitates removing the probe cover from the medical probe after use. The adhesive element can easily be removed from the probe with only one hand. It is yet another object of the invention to develop a protective cover set, whereby the probe cover can be attached securely to the medical probe without components that can be lost or that can shift relative to the probe cover during use.

The present invention may also provide an integrated and fully disposable protective cover set.

In accomplishing the foregoing objects, there has been provided, according to the present invention, a protective cover set for covering a medical probe that may be inserted into an endocavity or used intraoperatively through an incision in a human or an animal body, said cover set comprising a probe cover made from a film material, said probe cover having a mouth end for inserting said probe and a closed end opposite to said mouth end; and an outer wrapper being joined to said probe cover, said outer wrapper covering at least a length of said probe; wherein the probe cover comprises an adhesive element connected to said mouth end of said probe cover. The outer wrapper may be joined to said probe cover by an adhesive. Alternatively, the outer wrapper may be joined to the probe cover by a heat sealing joint.

The adhesive element may form an integral part of the probe cover, such that the adhesive element is irremovably connected to the rest of the probe cover. This may be accomplished by coating parts of the probe cover with an adhesive or by permanently attaching a separately manufactured adhesive element to the probe cover.

In one embodiment of the invention, the pressure-sensitive film is provided one part of the adhesive element. This yields an easy to use probe cover pack that is easy to manufacture.

In order to provide a pressure-sensitive film that can be easily grabbed, the pressure-sensitive film may have an elongate shape having two narrow sides and two long sides, wherein the pressure-sensitive film is connected to the mouth portion of the probe cover at one of its narrow sides. Connecting one narrow side of the pressure-sensitive film leaves both long sides and the remaining small side free so that the pressure-sensitive film can be easily picked.

To further ease the handling, the adhesive element may comprise an area that is not covered by the adhesive and which is located opposite to that narrow side which is connected to the probe cover. A user may grab this part of the adhesive element for attaching it to the medical probe or to other parts of the probe cover.

To facilitate production, the pressure-sensitive film can be connected to a portion of the probe cover by means of a heat sealed joint or a weld joint. Alternatively, the pressure-sensitive film may be connected to a portion of the probe cover by permanent adhesive.

For easy handling, the pressure-sensitive film may be at least partly covered by a liner. This liner may be a separable component of the protective cover set. Alternatively, the liner may be formed by a part of the probe cover or the outer wrapper. For example, the pressure-sensitive film may adhere removably to a portion of the probe cover at its mouth end so that this part of the probe cover represents the liner of the adhesive element.

It is possible that the adhesive element is located at an outside surface of the probe cover and adheres to an inside surface of the outer wrapper thus joining the outer wrapper to the probe cover. When the medical probe is inserted into the probe cover through its mouth, it exerts a pressure on the probe cover so that the adhesive element is detached from the outer wrapper and is attached to the medical probe. The outer wrapper is thus detached from the probe cover and can be removed easily.

The pressure-sensitive film has a film length and the mouth end has a circumference, wherein the film length may be comprised in an interval ranging from about a half of the circumference to about a double of the circumference. It has turned out that a pressure-sensitive film of such length is especially easy to handle and to manufacture.

The adhesive element may be capable of adhering removably to a medical probe and is made of a plastic or metal material. Thus, the medical probe remains unaffected from the probe cover and there is no need to clean it after use.

The liner may be made from an opaque plastic material. Especially when the probe cover or the other components of the protective cover set are made from a transparent material, it is easy to distinguish the liner from the other components.

BRIEF DESCRIPTION OF THE DRAWINGS

The foregoing and other objects, aspects, and advantages will be better understood from the following detailed description of a preferred embodiment of the invention with reference to the drawings, in which.

DETAILED DESCRIPTION OF THE DRAWINGS

Figure 1:
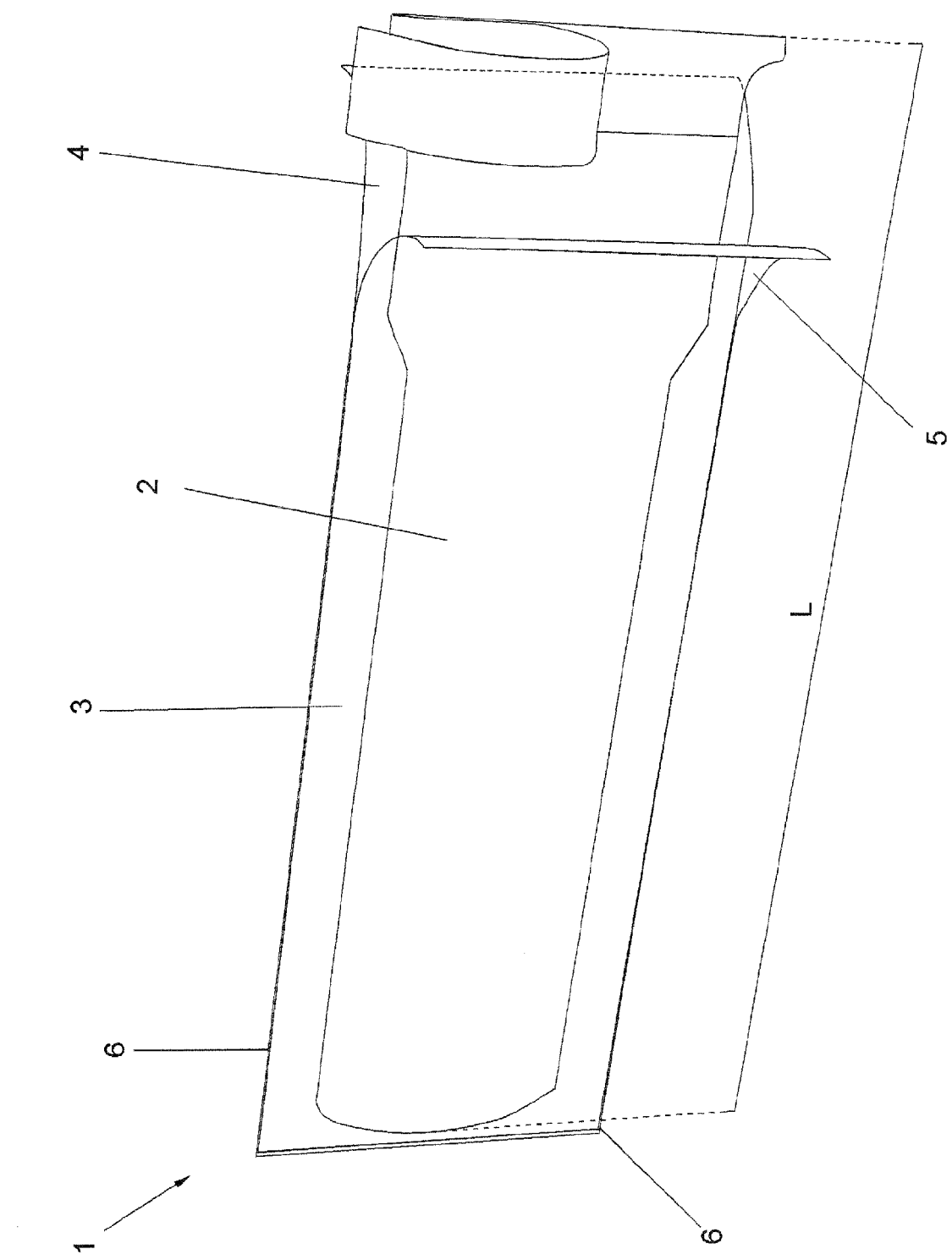
FIG. 1 is a perspective view of a protective cover set according to the invention.

Referring now to the drawings, and more particularly to FIG. 1, there is shown a protective cover set 1 for a medical probe, e.g. an ultrasound probe, comprising a probe cover 2 and an outer wrapper 3. Outer wrapper 3 consists of a lower ply 4 and an upper ply 5, both being made of a transparent flat film material and both being joined along their lateral edges by adhesive joints 6. Lower ply 4 and upper ply 5 form a sheath that ensheathes probe cover 2 along approximately three quarters of a length L of probe cover 2.

Figure 2:
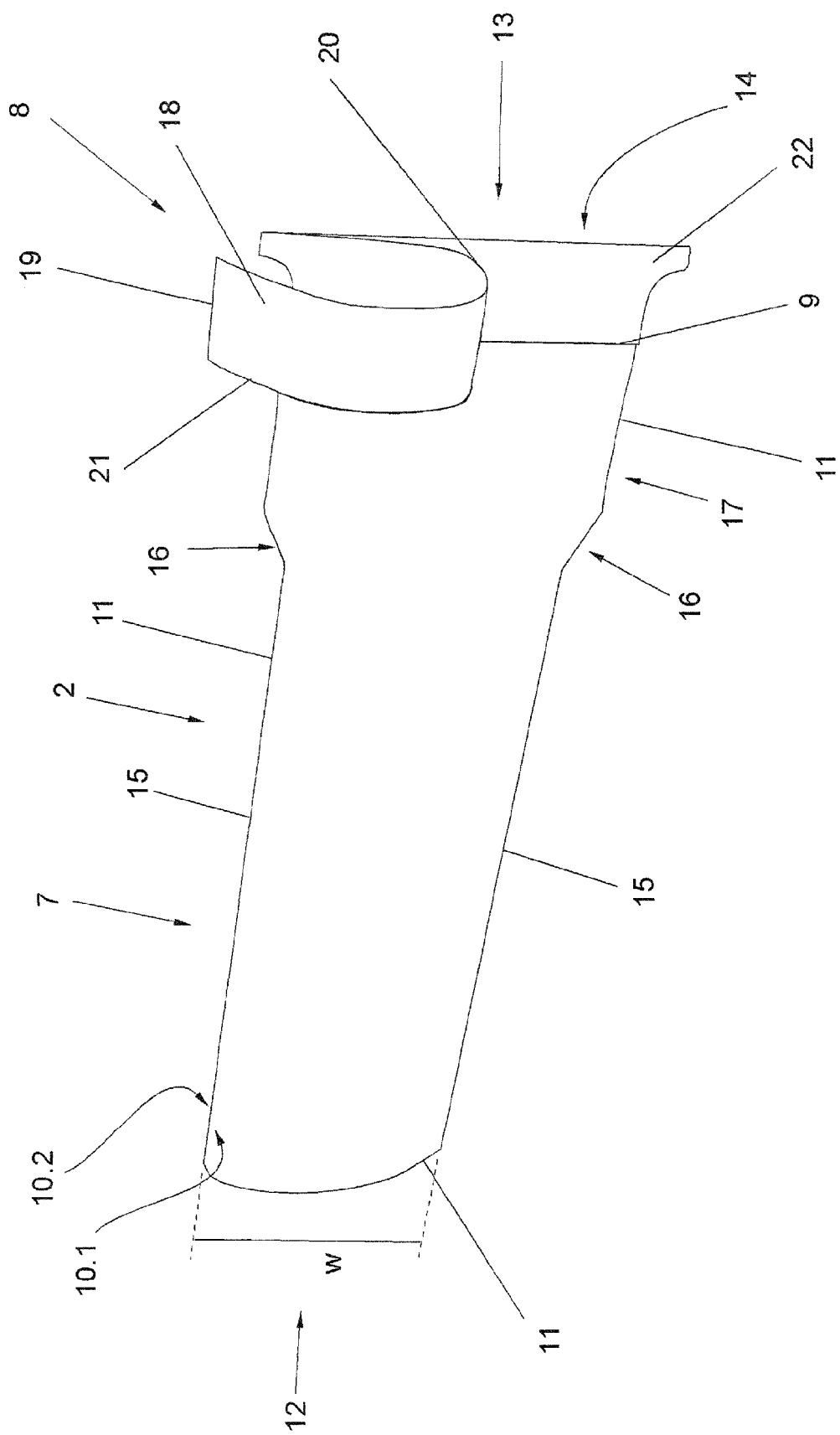
FIG. 2 is a perspective view of a probe cover of the protective cover set according to FIG. 1.

Referring now to FIG. 2, there is shown the probe cover 2, which comprises a main body 7 and an adhesive element 8. Main body 7 and adhesive element 8 are joined together by a heat sealed seam 9. In an alternative embodiment, main body 7 and adhesive element 8 may be joined together by a permanent adhesive.

Main body 7 consists of a first ply 10.1 and a second ply 10.2, both made of a transparent flat film material such as polyethylene, which are cut in suitable shape and joined together along their edges by means of a heat sealed seam 11.

Probe cover 2 has a closed end 12 and a mouth end 13 which is opposite to the closed end 12. At its mouth end 13, first ply 10.1 and second ply 10.2 are not joined so that a mouth 14 is formed for inserting a medical probe (not shown).

In the vicinity of closed end 12, probe cover 2 has a constant width w, the area of constant width being bordered by two essentially straight parallel edges 15. An outwardly tapering section 16 leads to a wider section 17 adjacent to mouth 14. Wider section 17 facilitates insertion of an ultrasound probe into probe cover 2.

Adhesive element 8 is positioned towards the mouth end 13 and forms a part of mouth 14. Adhesive element 8 comprises a pressure sensitive film 18 which has an elongate shape and a first narrow side 19.1, a second narrow side 19.2, a first long side 20, and a second long side 21. Pressure sensitive film 18 is heat sealed or adhered to liner 22. Before use, adhesive film 18 is covered by a liner 22 which is heat sealed to main body 7 by heat sealed seam 9.

FIG. 2 shows pressure-sensitive film 18 being partly peeled off from liner 22. Both, pressure-sensitive film 18 and liner 22 are made from an opaque polyethylene film material and thus contrast main body 7 which is made of a transparent polyethylene film material.

At its mouth end 13, probe cover 2 has a circumference which equals two times the width of first ply 10.1. Pressure-sensitive film 18 has a film length, which may equal the width of first ply 10.1 at the mouth end 13. However, pressure-sensitive film 18 may be covered by a separable liner and may have a length that is significantly longer than the width of first ply 10.1. For example, the length of pressure-sensitive film 18 may be two or three times the width w. Before use, probe cover 2 is entirely covered by outer wrapper 3 thus protecting it against dirt and dust. To ease handling, the outer wrapper 3 may be may be backed by a paper backing (not shown).

Figure 3A:
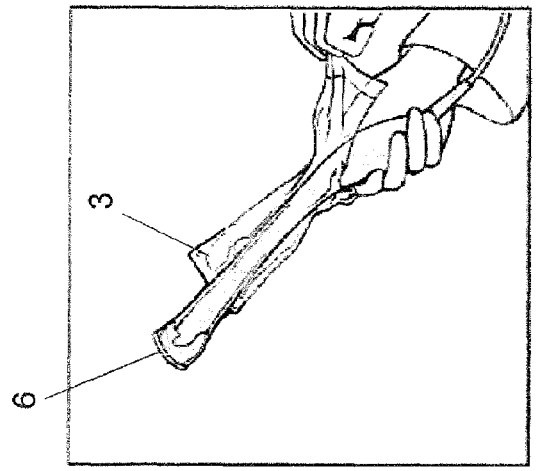
FIGS. 3a to 3f show the use of the inventive protective cover according to FIGS. 1 and 2 in a schematic sequence.
Figure 3B:
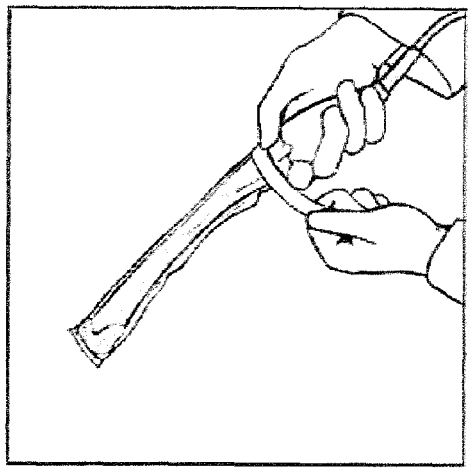
Figure 3C:
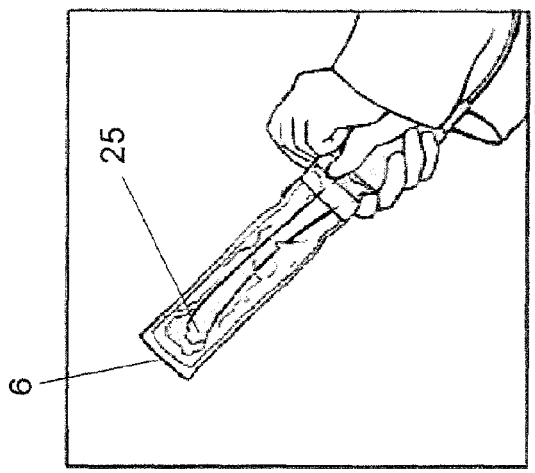

Referring now to FIGS. 3a to 3f, FIG. 3a shows an ultrasound probe 23, which is a medical probe, being inserted into mouth 14 of probe cover 2. Probe cover 2 may comprise a gel 24 at its closed end 12. Ultrasound probe 23 is inserted into probe cover 2 until a transducer head 25 of ultrasound probe 23 reaches the gel 24. Then, the adhesive joint 6 breaks such that the lower ply 4 and the upper ply 5 are separated. Outer wrapper 3 is then removed and probe cover 2 released, as shown in FIG. 3c.

Figure 3D:
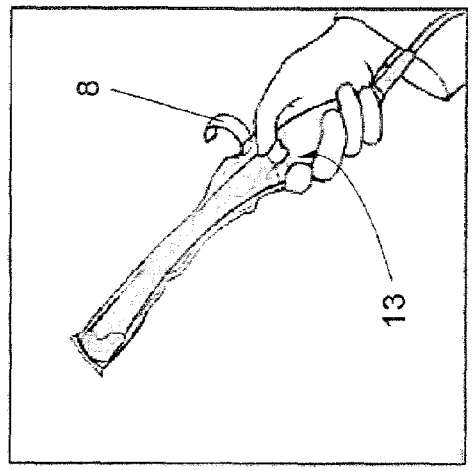
Figure 3E:
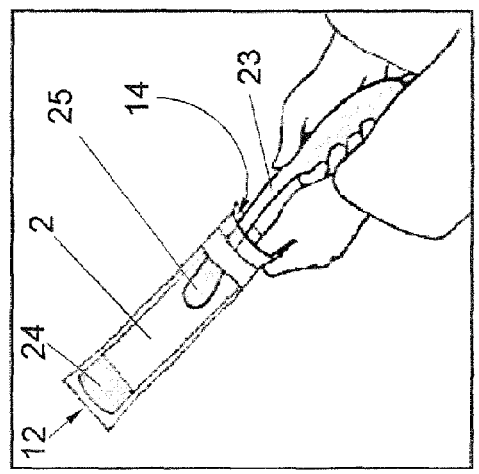
Figure 3F:
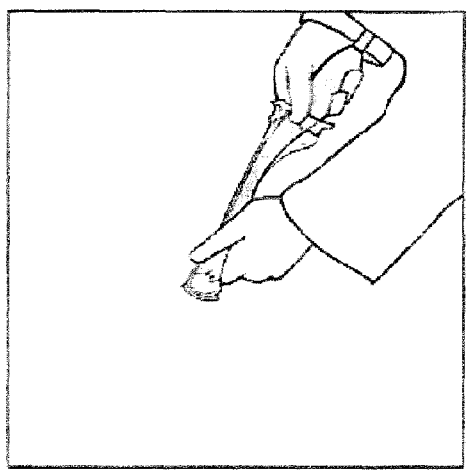

After removing gas bubbles by smoothing probe cover 2 over transducer head 25, as is shown in FIG. 3d, pressure-sensitive film 18 is peeled off the mouth end 13 of probe cover 2, as is shown in FIGS. 3e and 3f. Pressure-sensitive film 18 is than wrapped around probe cover 2 at its mouth end 13 and is thus firmly fixed to ultrasound probe 23.

While the invention has been described in terms of a single embodiment, those skilled in the art will recognize that the invention can be practiced with modification within the spirit and scope of the appended claims.

Having thus described my invention, what I claim as new and desired secure by Letters Patent is as follows:

1. A protective cover set for a medical probe comprising
   a probe cover made from a film material designated to be inserted into an endocavity or used intraoperatively in an incision of a human or an animal body, said probe cover having a mouth end with a mouth for inserting said probe and a closed end opposite to said mouth end; and
   an outer wrapper being joined to said probe cover, said outer wrapper covering at least a length of said probe cover;
   the probe cover comprising an adhesive element having a portion irremovably connected to said mouth end of said probe cover, and a portion of the adhesive element when peeled from said probe cover will wrap at least partially around the probe cover at the mouth end.

2. The protective cover set according to claim 1, said adhesive element comprising a pressure-sensitive film.

3. The protective cover set according to claim 2, said pressure-sensitive film having an elongate shape having two narrow sides and two long sides; said pressure-sensitive film being connected to a remainder of said probe cover at one of its narrow sides.

4. The protective cover set according to claim 2, said pressure-sensitive film being connected to said probe cover by means of a heat sealed joint or a weld joint.

5. The protective cover set according to claim 2, wherein said pressure-sensitive film is covered by a liner.

6. The protective cover set according to claim 3, where said pressure-sensitive film removably adheres to said mouth end of said probe cover.

7. The protective cover set according to claim 1, said adhesive element is located at an outside surface of said probe cover and removably adheres to said outer wrapper thus joining said outer wrapper to said probe cover.

8. The protective cover set according to claim 3, said long side of said pressure-sensitive film having a film length and said mouth end having a circumference; said film length being between about half of said circumference to about double of said circumference.

9. The protective cover set according to claim 1 said portion of the adhesive element when peeled from said probe cover removably adheres to a medical probe made of a plastic material.

10. The protective cover set according to claim 5, said liner being made from an opaque plastic material.

* * * * *